US008357117B2

(12) United States Patent
Sokal et al.

(10) Patent No.: US 8,357,117 B2
(45) Date of Patent: Jan. 22, 2013

(54) DEVICE AND METHOD FOR DELIVERING AN AGENT INTO BREAST MILK WHILE BREASTFEEDING

(75) Inventors: David C. Sokal, Durham, NC (US); Stephen E Gerrard, Altrincham (GB); Elizabeth Kneen, Ottumwa, IA (US); Ryan Hubbard, Kingsport, TN (US); Geoff Galgon, Pasadena, CA (US); Tombozgani Banda, Chichiri (MW)

(73) Assignee: Family Health International, Durham, NC (US)

( * ) Notice: Subject to any disclaimer, the term of this patent is extended or adjusted under 35 U.S.C. 154(b) by 669 days.

(21) Appl. No.: 12/536,219

(22) Filed: Aug. 5, 2009

(65) Prior Publication Data

US 2010/0292637 A1 Nov. 18, 2010

Related U.S. Application Data

(60) Provisional application No. 61/086,560, filed on Aug. 6, 2008.

(51) Int. Cl.

| | |
|---|---|
| ***A61M 1/06*** | (2006.01) |
| *A61J 7/00* | (2006.01) |
| *A61J 17/00* | (2006.01) |
| *A61M 37/00* | (2006.01) |
| *A47G 21/18* | (2006.01) |

(52) U.S. Cl. ................ 604/76; 604/74; 604/77; 604/85; 426/85; 606/236

(58) Field of Classification Search .................... 426/85; 604/74, 76, 77, 85; 606/236
See application file for complete search history.

(56) References Cited

U.S. PATENT DOCUMENTS

| | | | | |
|---|---|---|---|---|
| 4,366,202 | A * | 12/1982 | Borovsky | 442/164 |
| 4,536,495 | A | 8/1985 | Bergwitz-Larsen et al. | |
| 5,029,701 | A * | 7/1991 | Roth et al. | 206/232 |
| 5,094,861 | A | 3/1992 | D'Auguste et al. | 426/85 |
| 5,127,903 | A * | 7/1992 | Mailot et al. | 604/77 |
| 5,638,769 | A * | 6/1997 | McIntyre et al. | 119/71 |
| 5,810,003 | A * | 9/1998 | Findlater | 128/203.12 |
| 6,109,538 | A * | 8/2000 | Villani et al. | 239/33 |
| 6,899,696 | B2 | 5/2005 | Morton et al. | 604/74 |
| 7,364,756 | B2 * | 4/2008 | Gabbay | 424/635 |
| 2002/0015697 | A1 | 2/2002 | Beckman et al. | |
| 2004/0006044 | A1 | 1/2004 | Barkan et al. | |
| 2005/0002921 | A1 * | 1/2005 | Rehberger et al. | 424/93.45 |
| 2005/0059927 | A1 * | 3/2005 | Buiatti | 604/74 |
| 2006/0042550 | A1 * | 3/2006 | Hoshiba et al. | 119/71 |
| 2007/0005006 | A1 | 1/2007 | Rosenfeld | |
| 2007/0010760 | A1 * | 1/2007 | Rosenfeld | 600/573 |

FOREIGN PATENT DOCUMENTS

| | | |
|---|---|---|
| CN | 101591695 A | 12/2009 |
| DE | 1957739 | 5/1971 |
| JP | 2002003365 | 1/2002 |
| WO | WO2004/082558 | 9/2004 |

* cited by examiner

*Primary Examiner* — Nicholas Lucchesi
*Assistant Examiner* — Ian Holloway
(74) *Attorney, Agent, or Firm* — MacCord Mason PLLC

(57) ABSTRACT

A device for delivering an agent into breast milk while breastfeeding. In one embodiment, the device includes a breast shield modified to engage a non-woven material which has been impregnated with a milk soluble active agent such as sodium dodecyl sulphate (SDS). A lactating animal, e.g. a woman, uses this agent-delivering breast shield during breastfeeding to administer prophylactic or therapeutic agents to a suckling infant. The inventions are particularly well suited to preventing transmission of HIV virus from mother to child. Alternatively, the agent-laden material could be used with a baby bottle nipple or pacifier.

42 Claims, 6 Drawing Sheets

DEVICE AND METHOD FOR DELIVERING AN AGENT INTO BREAST MILK WHILE BREASTFEEDING

Similar technology is disclosed in commonly owned and U.S. Provisional Patent Application No. 61/086,560, filed Aug. 6, 2008.

BACKGROUND (1) Field

The present inventions relate generally to drug delivery systems and, more particularly, to a device for use during breastfeeding to introduce agents directly into the milk stream.

(2) Related Art

Currently the World Health Organization recommends that, "when replacement feeding is acceptable, feasible, affordable, sustainable and safe, avoidance of all breastfeeding by HIV-infected mothers is recommended. Otherwise, exclusive breastfeeding is recommended during the first months of life." This is because using formula in low-resource settings has been shown to decrease infant survival due to increased numbers of deaths from diarrhea and malnutrition (Brahmbhatt, 2003). In terms of specific breastfeeding recommendations, the situation is ambiguous. Some of the most recent published data from a study of exclusive breastfeeding followed by rapid weaning in Zambia has shown no benefit for the intervention group compared to a control group that followed traditional breastfeeding practices. About 7% of infants in both groups became HIV infected via breast milk between four and 24 months of age.

Another recent study has shown that giving anti-retroviral medications (ARVs) to a breastfeeding infant could reduce HIV transmission. However, the use of ARVs may lead to the evolution of resistant viruses, which would complicate eventual treatment of acquired immunodeficiency syndrome (AIDS) in infants that become infected despite the use of prophylactic ARVs. Despite these issues, the most promising current strategy to prevent HIV transmission through breast milk appears to be prophylactic treatment of breastfeeding infants with ARVs.

It would be advantageous to prevent HIV without the use of ARVs and without interrupting normal breastfeeding patterns. One approach for protecting infants is to have mothers express their breast milk into a container, heat the breast milk, i.e. an abbreviated pasteurization process, and feed it to the baby using a spoon or a bottle. However, this disrupts normal breastfeeding patterns and is impractical and burdensome for mothers living in low-resource settings.

A number of inventions have proposed the use of a modified pacifier or baby bottle nipple to deliver liquid medications to an infant. However, the preparation of formulations for administration to infants as liquids is complex and time consuming, and putting medications in a fluid greatly reduces their stability and usually requires refrigeration.

It is to these and other problems that the instant disclosure is directed. In particular, Applicants have identified a need for devices capable of delivering therapeutic or prophylactic formulations during breastfeeding. In one embodiment, this device is simple to manufacture and use, lightweight, relatively inexpensive, discreet, and effective. Typically, such devices should be able to inactivate or kill HIV in breast milk in a way that is convenient and entails minimal disruption of breastfeeding. It would also be advantageous to have a method to prepare and store a medication in a dry form that does not require dissolution by a pharmacist before administration, and can be easily dissolved one dose at a time.

SUMMARY

The present inventions are directed towards devices and methods for delivering at least one agent into beast milk while breastfeeding. In one embodiment, the agent or agents include a prophylactic agent that can be produced and stored as a non-liquid formulation, for later use during breastfeeding.

Accordingly, one aspect of the inventions is to provide a breast shield with a hollow nipple, and a milk-soluble agent suspended on a matrix. Preferably the breast shield is reusable.

Another aspect of the inventions is to provide an agent which is safely ingested, and provides anti-viral, preferably anti-HIV, properties. This agent can be a variety of substances including drugs, nutrients, polymers, metals and surfactants including sodium dodecyl sulfate.

Yet another aspect of the inventions is to provide a matrix which is constructed of a substrate suitable for holding an appropriate amount of agent, yet allows milk to pass through without significantly affecting the flow rate. This matrix is preferably inert, safe, lightweight and relatively inexpensive. Preferably, this matrix is a non-woven material.

In another aspect of the inventions, disease is prevented during breastfeeding by providing a breast shield for a lactating mother which includes an inlet for milk, a matrix downstream of the inlet, and an outlet defined by the breast shield which is suitable for suckling.

Still another aspect of the inventions is a method of delivering an agent into breast milk wherein a matrix is engaged with a breast shield, the breast shield is positioned on the breast of a lactating mother, and the baby suckles the breast shield.

These and other aspects of the present invention will become apparent to those skilled in the art after a reading of the following description of the preferred embodiments, when considered with the drawings.

DESCRIPTION OF THE PREFERRED EMBODIMENTS

Figure 1:
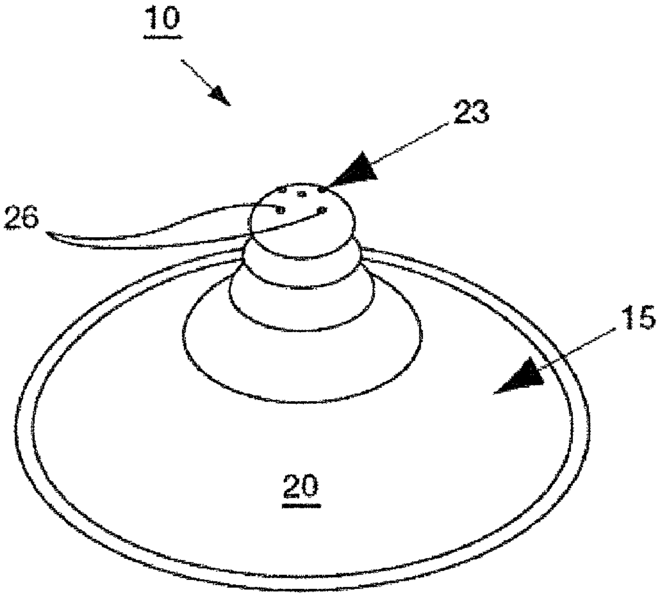
FIG. 1 is a perspective view of a breast shield delivery device constructed according to the present inventions.
Figure 2:
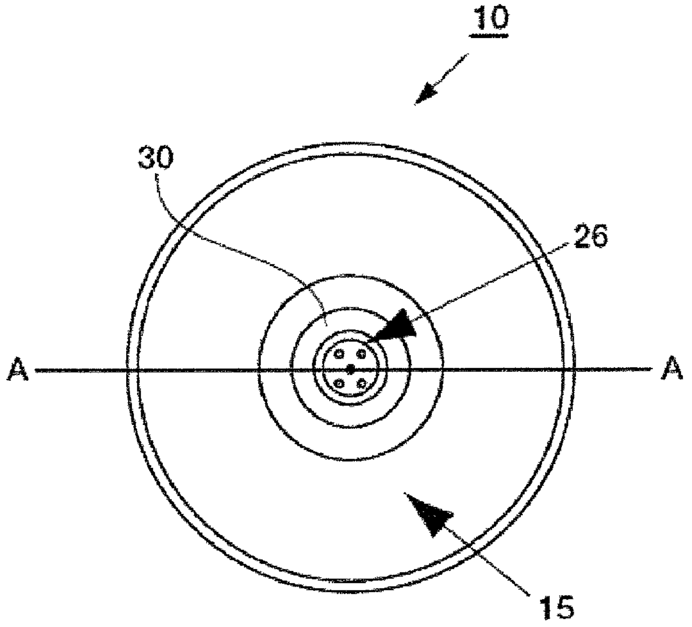
FIG. 2 is a top view of the breast shield delivery device.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, a delivery device, generally designated as 10, is shown. In this embodiment, delivery device 10 includes breast shield 20, having breast portion 15, and external nipple portion 23, which defines hollow nipple portion 22 (shown in FIG. 4). A matrix 30 (shown in FIG. 3) is positioned within hollow nipple portion 22. At least one hole 26 is defined in external nipple portion 23.

Figure 3:
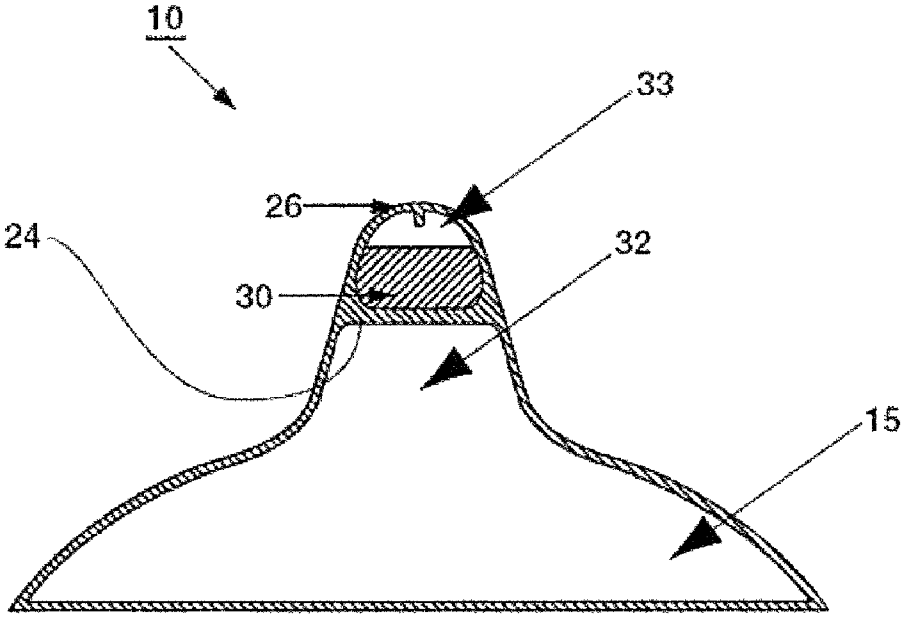
FIG. 3 represents a cross-sectional view of the breast shield delivery device taken along line A-A of FIG. 2.
Figure 4:
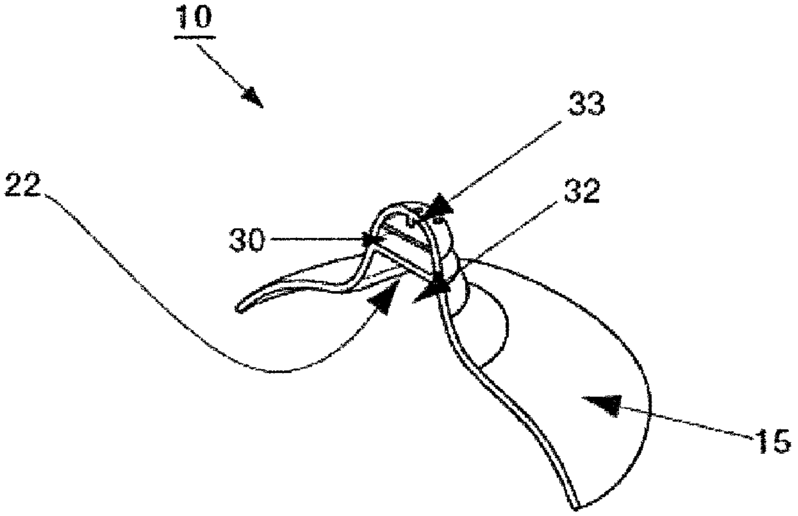
FIG. 4 represents a rotated cross-sectional view of the breast shield delivery device taken along line A-A of FIG. 2.

In use, breast portion 15 would be in contact with the lactating breast, the suckling child would latch onto nipple portion 23 and milk would travel through matrix 30 and holes 26 to the child. In the present inventions, the delivery device 10 may further include a retention lip 24 for holding matrix 30 in position, as best shown in FIG. 3.

The matrix of the present inventions can be in the form of a woven or non-woven textile, impregnated with various agents, or it can consist of a textile or porous plastic structure that holds in place an active agent in the form of one or more dissolving tablets. Where a textile is impregnated with various agents, it is preferred that the agent is air dried, but heat fixing and freeze drying are also possible. Agents to be delivered by the matrix can include antimicrobial agents including antiviral agents, micronutrients, or other medications or therapeutic agents. During the passage of breast milk or other fluid through the matrix, the fluid can also be disinfected by contact with a specially treated textile material.

A multitude of approaches and devices for preventing HIV transmission were considered before arriving at the preferred inventions disclosed herein. One approach was to use abbreviated pasteurization wherein mothers would express their breast milk into a container, heat the breast milk, i.e. an abbreviated pasteurization process, and then feed it to the baby using a spoon or a bottle. However, it was expected that this would disrupt normal breastfeeding patterns and women would need to have frequent access to a source of cooking heat. The expense of a fueling a stove or cooking fire virtually around the clock would make this impractical and/or too costly for most mothers living in low-resource settings. Also, there are severe social stigmas associated with HIV and mothers might be hesitant to treat their breast milk in a manner likely to be perceived as unusual by a casual observer because doing so could evoke suspicion.

Another approach was to treat expressed milk in bottle with a chemical such as sodium dodecyl sulphate (SDS), also known as sodium lauryl sulfate, to kill HIV, then to feed the treated milk to the baby. This approach would overcome the heat requirement problem, but would still be very disruptive to normal breastfeeding and would be time consuming and burdensome. Also, it could evoke suspicion in the casual observer.

Still another approach was an armpit breast pump that would include a conventional plastic breast milk collector piece, but rather than using an electric pump, the woman could squeeze and release a bulb with one way valves under her armpit to generate suction. Energy would be supplied by the mother raising and lowering her upper arm and squeezing the bulb against the side of her rib cage. After passing through the bulb, the breast milk would return via a tube to be delivered to the baby in front of the breast, so that the baby would appear to be breastfeeding. A metered delivery system would add SDS or another chemical to the milk in a reservoir, just before it was taken by the infant. However, the device would be relatively complex and costly and the parts would need to be regularly disassembled and cleaned. Also, the pumping upper arm action could evoke suspicion.

Still another approach was an electrical option for the armpit breast pump. It would include the use of battery-stored solar energy to heat the milk as it passed through a reservoir associated with the arm-pit pump. However, solar collectors and batteries needed to even briefly heat the average amount of fluid produced by a breastfeeding woman, approximately 800 gm per day, to a temperature of about 60° C., would be extremely costly. Further, the batteries would probably be too heavy and inconvenient for a mother to carry. Moreover, it could evoke suspicion.

Still another approach was a shaker bottle with magnets, into which a mother would express her milk then shake the bottle. Upon shaking, the magnets would induce an electromagnetic field in an externally insulated coil surrounding the bottle, and the externally insulated coil would energize heating coil to heat the milk. A number of emergency flashlights have mechanisms like this. However, the amount of energy needed to heat/disinfect breast milk would be difficult to generate using this mechanism, and it would be disruptive to breastfeeding. Also, it could evoke suspicion.

Still another approach was a bra with an electrical pump. A compact electrical breast pump would pump breast milk into a small reservoir where it could be briefly heated or mixed with a chemical such as SDS, and then passed along a tube to the breastfeeding baby. However, in low-resource settings, there is often no access to electricity, or access is unreliable. Further, many women need to breast feed their babies while they take a break from working in their families agricultural fields, where electricity would not be available.

Still another approach was a breast shield with a matrix, basically as set forth in this disclosure. This approach was initially dismissed in view of what was expected to be insurmountable obstacles. Specifically, it was initially believed a breast shield with a matrix would not be functional because: (a) the matrix wouldn't be able to deliver enough chemical; (b) the matrix would obstruct milk flow; (c) the chemical would be too toxic for the mother's breast or for the baby; (d) the chemical would not kill HIV rapidly enough; and/or (e) the chemical would be released too quickly. However, after extensive experimentation, it was found that this approach of the present inventions yielded unexpectedly good results and the technical obstacles could be overcome.

The relative benefits and drawbacks of the various ideas are set forth below in TABLE 1 wherein 5=most favorable, e.g. similar to normal breastfeeding or lowest cost; and 1=least favorable, e.g. unlike normal breastfeeding or highest cost.

TABLE 1

COMPARISON OF VARIOUS DEVICES

| | Description | Similarity to Normal Breast-feeding | Cost (time and money) | Ease of Use | Breast Pumping Needed | Heat Energy Needed |
|---|---|---|---|---|---|---|
| 1) | Abbreviated pasteurization | 1 | 1 | 1 | Y | Y |
| 2) | Treatment in bottle with a chemical | 1 | 2 | 1 | Y | N |

TABLE 1-continued

COMPARISON OF VARIOUS DEVICES

| | Description | Similarity to Normal Breast-feeding | Cost (time and money) | Ease of Use | Breast Pumping Needed | Heat Energy Needed |
|---|---|---|---|---|---|---|
| 3) | Armpit breast pump and chemical | 2 | 3 | 2 | Y | N |
| 4) | Armpit breast pump and electrical heating | 2 | 1 | 2 | Y | Y |
| 5) | Shaker bottle | 1 | 1 | 2 | Y | Y |
| 6) | Bra with reservoir and electrical pump | 3 | 2 | 2 | Y | N |
| 7) | Breast shield with matrix | 5 | 4 | 4 | N | N |

Several agents were considered before settling on the preferred embodiments: copper, monoclonal antibodies, and surface active chemistry. With respect to copper, a 10-cm column filled with copper impregnated textile was shown to be effective for inactivation of HIV in culture media. However, this amount of matrix would probably not be feasible for milk, as the matrix is likely to become clogged with organic components of the milk, and would thus become too difficult for a suckling infant to obtain milk. Further, the size and expense of the matrix would pose difficulties.

Regarding monoclonal antibodies, using a sehparose filter with a disease binding agent would selectively segregate viral particles, but a final design was never achieved. Specifically, attaching anti-HIV monoclonal antibodies to a sepharose filter and putting the sepharose filter in a breast shield type device seemed untenable because of insufficient contact time given that the half-life for viral removal through a column with continuous recirculation is about 2.5 hours.

Likewise, an agent based on surface active chemistry would have inadequate contact time with virus particles. In addition, the chemically-reactive groups would probably become saturated via reactions with other (non-HIV) components in the milk.

Four important aspects of the present inventions include:

(1) Killing HIV During and after Passage Through the Matrix.

Using an agent that is edible, i.e. recognized as a non-toxic food additive, but still kills HIV, provides for the release of the agent into the breast milk, so that the killing action does not have to occur instantaneously during the flow of the breast milk through the matrix. To achieve a high level of virus elimination, the killing action may occur over several seconds to a few minutes, and could occur while the breast milk is in the infant's mouth, esophagus or stomach. Since food is held in the stomach for acidification and achievement of osmotic equilibration before being released into the intestines, it is likely that any virus that reaches the stomach would be killed there and would not enter the intestines. Preventing viable HIV virus from entering the intestines is potentially important given that HIV might be transmitted in the intestines.

(2) Sufficient Dosage is Possible.

Given that a concentration of about 0.05% to 0.1% concentration of SDS is sufficient to kill HIV, the amount needed for a breastfeeding mother would be 50 mg to 100 mg of SDS per 100 g of breast milk to give a concentration of 0.05% to 0.1%. A breastfeeding baby drinks on average 800 g of breast milk per day, with the more productive breast producing about 500 g per day. Accordingly, for 500 g of breast milk, 250 to 500 mg of SDS would be needed to be released continuously from a single matrix. Alternatively, in order to allow for the range of milk production rather than just the average, the matrices could be changed more than once per day. Thus one matrix would need to treat one quarter of the maximum of a day's milk production. The upper limit of the range from the more productive breast would require that one matrix treat 769/2 or about 350 g of milk, requiring about 175 to 350 mg of SDS per matrix, with the use of one or more matrices per day for each breast.

It was an unexpected result that, without the use of any excipients, a non-woven material could be dipped into an SDS solution to achieve significant loading and release of SDS. Specifically, a piece of soft non-woven material was dipped in a 20% solution of SDS, then dried on a drying rack. After drying, the material was hard and stiff, and felt like a piece of cardboard. It appeared unlikely that the resulting material would even be permeable to water. However, it was unexpectedly found that there was virtually no resistance to fluid flow when a 3 mm thick disk was positioned in a standard 10 ml syringe, and water was gravity fed into the top of the syringe where the plunger would normally be positioned. Moreover, the SDS was rapidly released into the water.

(3) Slow Release is Possible.

It is possible to incorporate slow release technologies, including low cost excipients that are approved for oral administration, to achieve slow release of sufficient quantities of SDS for achieving a concentration on the order of 0.05% to 0.1% in up to 350 or 700 g of breast milk, i.e. for twice or once daily matrix replacement, respectively.

(4) Benefits of Breastfeeding are Retained.

It is also very important that the invention not significantly negatively affect the nutritional and immunological benefits, or volume, of breastmilk, nor the emotional benefits to mother and child of breastfeeding itself.

The present inventions preferably include at least two major fields of use: preventing HIV (or other viruses) from being transmitted through breast milk; and/or delivery of medications or nutritional aid/supplements. For the first field of use, preventing HIV transmission (or transmission of other viruses) through breast milk, a textile disk may be made of women or non-woven textile materials, and may be impregnated with various chemicals that inactivate HIV, such as SDS. A preferred method to make the device within the scope of this invention is to prepare a solution of SDS, preferably including a delay-release excipient such as hydroxypropylmethylcellulose (HPMC), saturate a non-woven material with the solution, dry the solution-laden material, cut the dried material (the matrix) into appropriate size disks, and package in blister packs.

Figure 5:
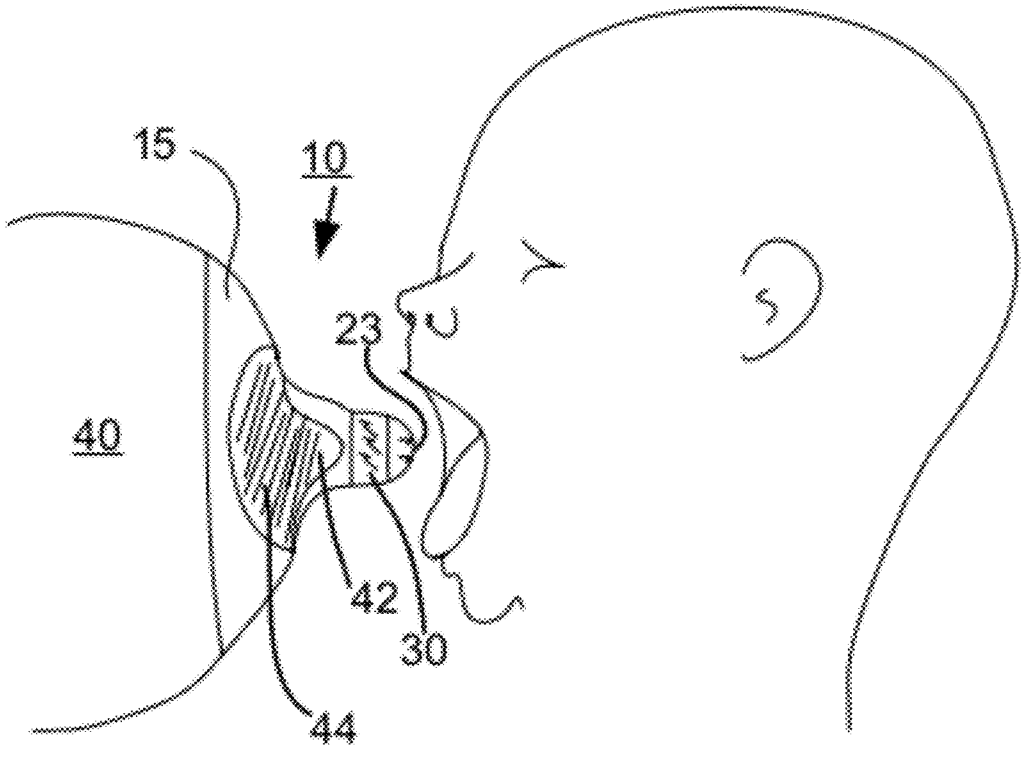
FIG. 5 depicts a baby preparing to suckle on the breast shield delivery device which is positioned on a lactating breast.

In one embodiment, a lactating mother opens a blister pack, inserts matrix 30 into hollow nipple portion 22 and secures it past retention lip 24. The mother places delivery device 10 over her breast 40, aligning her nipple 42 and areola 44 inside hollow nipple portion 22, and allows the suckling baby to latch onto external nipple portion 23, as shown in FIG. 5. She then feeds her baby as normal, with milk exiting nipple 42, passing through matrix 30, exiting holes 26, and entering the baby's mouth. Matrix 30 is preferably replaced periodically, for example once or twice per day, depending on the exact parameters of the particular active agent and excipients.

Microbicidal agents such as copper or silver could be incorporated into the matrix to provide catalytic or synergistic effects. It is also possible to incorporate a non-leaching, permanently microbicidal polymeric coating. In particular, hydrophobic polycations can be covalently attached onto the surface of the material or matrix, thereby providing a very large surface area for microbicidal action.

For another embodiment, the textile material, preferably a non-woven, may be impregnated with therapeutic formulations, including but not limited to orally administered pharmaceuticals, antibiotics, analgesics, CNS drugs, vitamins, minerals, micronutrients, probiotics, anti-retrovirals, proteins, copper, copper derivatives and combinations of one or more. It is common practice to administer antibiotics to infants via syrups. However, preparing syrups for infants is expensive, time consuming and leads to a much shorter half-life of drug stability compared to a drug in the dry state. With the present inventions, a pharmaceutical company could prepare a matrix with the desired agent, optionally including various flavoring agents, and a pharmacist could easily dispense the matrix to a mother without the need for syrup preparation. This could be done for medications requiring one-time or limited dosages as well.

Since infants of various weights and ages require different doses of many therapeutic agents, thin disks could be prepared such that each disk contains a certain amount of drug, e.g. 10 mg, and the dosage could be changed by changing the number of disks to be used. Thus, rather than prescribing a certain number of teaspoons of a medicine, a doctor could prescribe the use of a certain number of disks, e.g. four disks every six hours, in order to deliver a dosage of 40 mg every six hours.

An important advantage of this method of drug delivery is that the drug is maintained in the dry state prior to administration. Another advantage of using multiple disks within the device is that one disk could contain a flavoring agent. With this approach, the acceptability of a medication for infants could be improved by offering the mother/child a choice of flavors. With a separate flavor disk, a child's preference could easily be satisfied without having to produce a separate formulation for each flavor. It should also be noted that edible inks could be used to indicate the flavor or ingredients present on each disk in order to reduce the chance of medication error.

Devices according to certain embodiments of the invention may be manufactured, at least in part, using traditional breast shields. An example of a commercially available breast shield is the "Contact Nipple Shield, 24 mm Standard" model #67203 made by Medela Inc., of McHenry, Ill. Other breast shields, including those with cutouts to increase areola exposure, and those which are butterfly shaped, are also suitable for facilitating the present inventions. Traditional breast shields are known in the art, and may also be referred to as "nipple shields".

Figure 6:
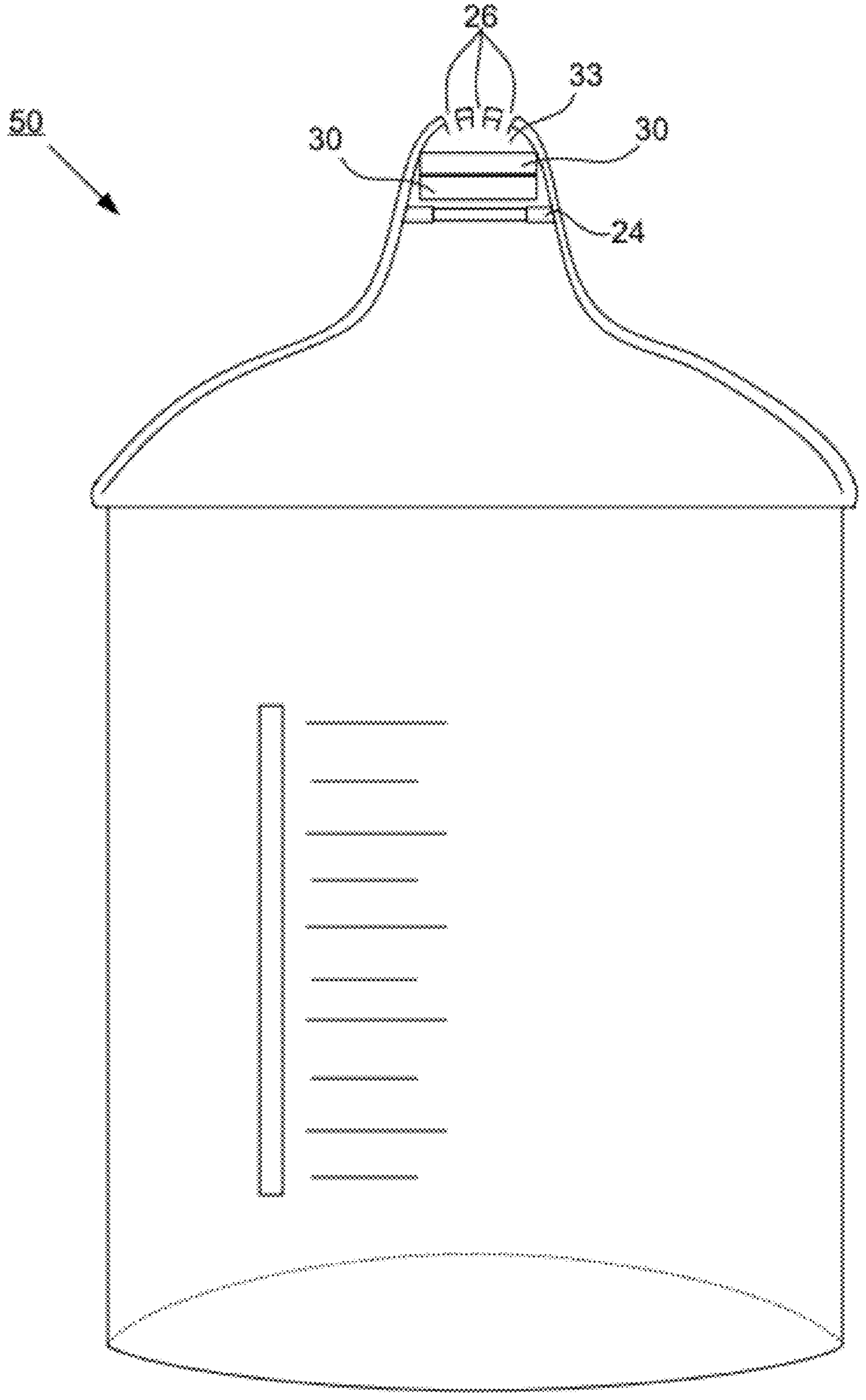
FIG. 6 depicts a baby bottle delivery device.
Figure 7:
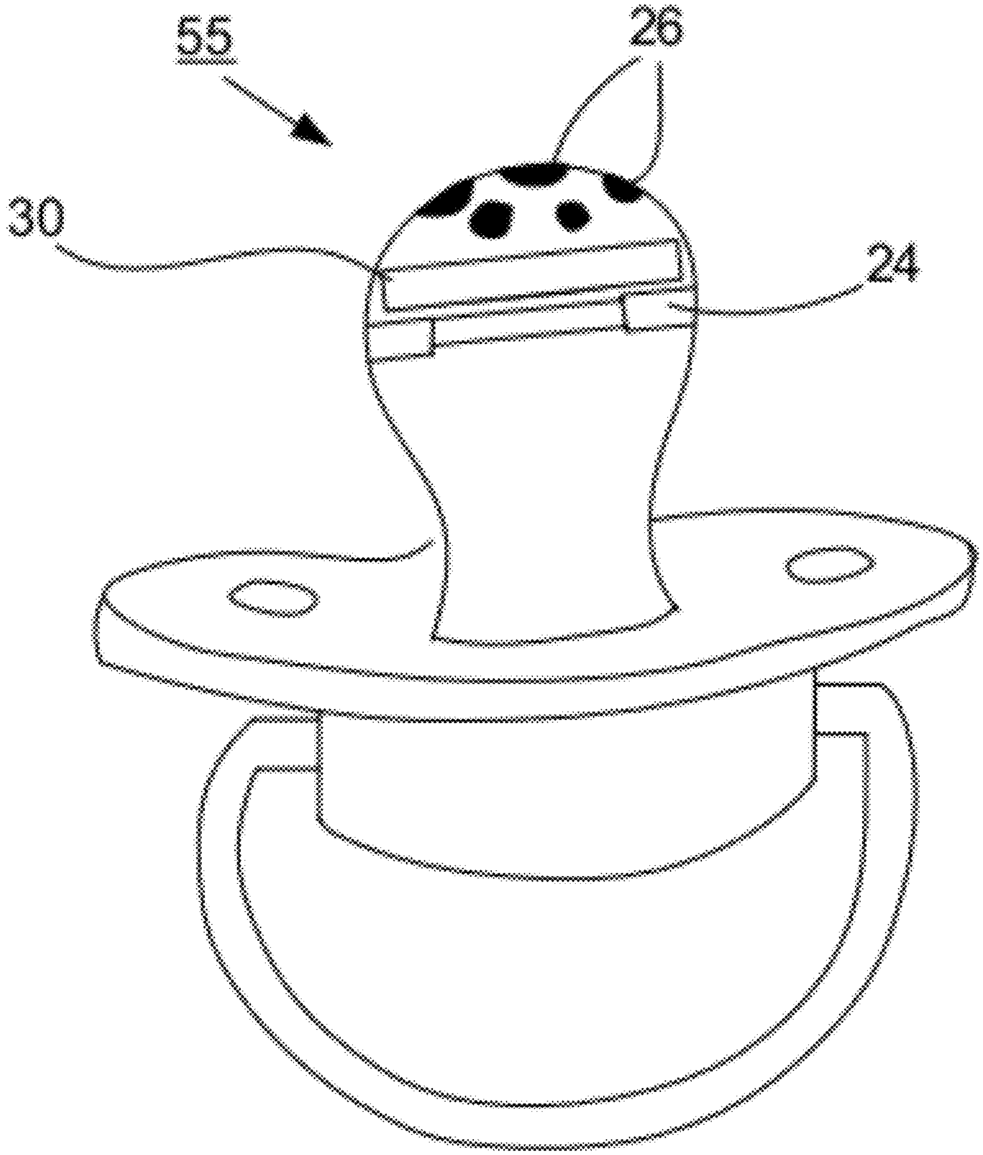
FIG. 7 depicts a pacifier delivery device.

While the present inventions are preferably geared towards breastfeeding, it is also possible to utilize the matrix technology within other vehicles such as baby bottles or pacifiers. For example, a matrix could be inserted into the hollow nipple portion of a baby bottle. If the matrix technology is used with baby bottle nipple 50, as shown in FIG. 6, it is preferred that baby bottle nipple 50 is modified to include a retention lip 24. It is also possible to insert at least one matrix 30 into a modified pacifier 55 including holes 26 and retention lip 24 as shown in FIG. 7. Saliva would act as the solvent in this embodiment. These alternative embodiments could be particularly useful where a breastfeeding baby rejects a breast shield, for example because they have been exclusively breast fed without a shield.

Further, while various embodiments of the invention are described primarily in relation to human mothers and babies, embodiments may be equally suited to veterinary uses, including shields, bottles, and pacifier-like devices for, e.g., companion and livestock animals.

It is also possible to impregnate the fibers of a textile material with an active agent at the time of manufacture of the textile fibers. For example, some melt-spun textile fibers can be prepared at temperatures as low as 125° C., and the trace elements or some pharmaceutical active agents may be robust enough to withstand this temperature, especially if an ambient atmosphere of nitrogen is used to prevent oxidation of the active agent.

Yet another embodiment utilizes nanofiber textile materials in order to increase the effective surface area of the porous material. With the use of nanofibers, the surface area of one gram of nanofibers may be as great as 500 square meters, compared to about one to 10 square meters per gram of conventional textile fiber. This approach could be combined with other approaches mentioned herein to improve the antimicrobial or drug delivery effectiveness of the invention.

Figure 8:
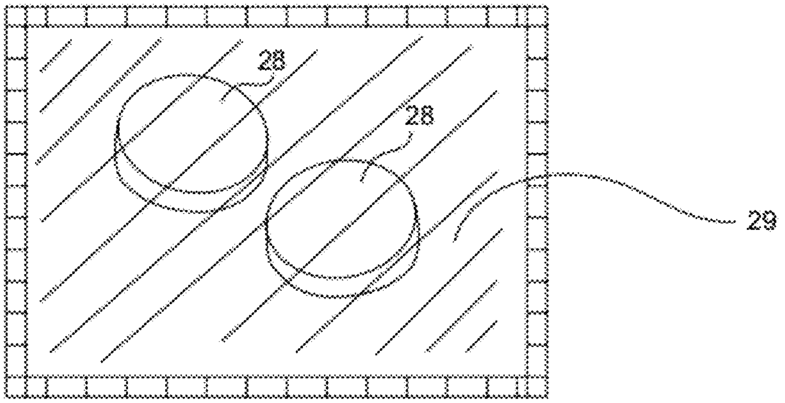
FIG. 8 depicts a porous container delivery device.

Still another embodiment, shown in FIG. 8, is to place a small tablet or multiple small tablets 28 (or matrix/matrices 30) within a porous container 29. Porous container 29 could be made of nonwoven or woven textiles, or of plastic, and be shaped like a small pillow or tea bag in a variety of shapes including rectangles (shown), or circles, squares or triangles (not shown) Alternatively, porous container 29 could be constructed of silicone with holes, with the silicone advantageously securing tablets. Container 29 is preferably sufficiently porous to permit fluid flow, thereby facilitating dissolution of the active agents in the tablet(s) 28 as the fluid passes through. The speed of dissolution of the tablets could be controlled by formulation of the tablet itself, as well as by the material used to construct porous container 29 itself. In use, tablets 28 could be placed in porous container 29 by the pharmaceutical manufacturer, pharmacist, or end user.

Figure 9:
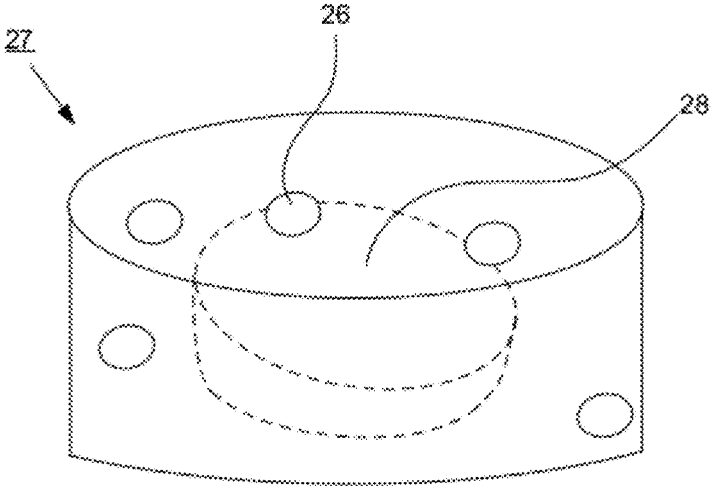
FIG. 9 depicts a cartridge delivery device.

In another embodiment, shown in FIG. 9, non-textile disk-shaped cartridge 27, which defines holes 26, contains a solid drug formulation, such as dissolving tablet 28. Cartridge 27 may or may not include a covering layer of textile or other material, with the latter depicted in FIG. 9.

In use, tablet-loaded porous container 29, as shown in FIG. 8, or tablet-loaded cartridge 27, as shown in FIG. 9, could be fitted past retention lip 24 in the various delivery devices (ie delivery device 10, bottle 50, and pacifier 55) in the same manner matrix 30 would be positioned.

It is also possible to combine matrices of different compositions to achieve more than one purpose. For example, if an embodiment is used to deliver a medication with water as the fluid rather than milk, in an area where water may be contaminated with infectious organisms, one matrix could be coated with a non-leachable antimicrobial or antiparasitic, and a second matrix could be used to deliver a medication. FIG. 6 depicts baby bottle nipple 50 with two matrices 30, but it should be understood that two or more matrices could likewise be used with breast shield 20 or pacifier 55.

Yet another embodiment is to place matrix (or matrices) 30, tablet-loaded porous container 29, as shown in FIG. 8, or tablet-loaded cartridge 27, as shown in FIG. 9 in fluid, for example a glass of milk or water. When the active ingredient is finished diffusing into the fluid, the spent matrix 30, porous container 29 or cartridge 27 would be removed, and the liquid consumed. This is potentially useful where pills are not well tolerated, but dispersing, storing or administering liquid-form medications is not practical.

In still another embodiment, the device would include a color indicating system to show that the agent has been delivered, or that the agent has been depleted. For example, an excipient of matrix 30 could include red dye. Thus, the matrix would appear red when excipient and active ingredient were present, but without color when the excipient and active ingredient had been dissolved. This would indicate to the user when it was time to replace matrix 30.

Certain modifications and improvements will occur to those skilled in the art upon a reading of the foregoing description. By way of example, mesh could be substituted for holes 26. Also, the nipple of the breast shield could be directly impregnated with the agent, thereby creating a disposable all-in-one agent-eluting shield Also, a breast shield could be built into a bra, optionally including a nipple which is retractable into the bra cup.

It should be understood that all such modifications and improvements have been deleted herein for the sake of conciseness and readability but are properly within the scope of the following claims.

We claim:

1. A device for delivering an agent into breast milk while breastfeeding, said device comprising:

(a) a breast shield with a hollow nipple, said hollow nipple including a retention lip protruding inwardly into said hollow nipple; and (b) at least one matrix impregnated with at least one milk-soluble agent, said matrix positioned within said hollow nipple, occupying substantially the entire cross section of said hollow nipple, and secured by said retention lip.

2. The device of claim 1, wherein said breast shield and said matrix are readily separable.

3. The device of claim 1, wherein said milk-soluble agent is Generally Recognized As Safe (GRAS).

4. The device of claim 1, wherein said milk-soluble agent is a surfactant.

5. The device of claim 4, wherein said milk-soluble agent is an alkyl sulfate.

6. The device of claim 5, wherein said milk-soluble agent is sodium dodecyl sulfate.

7. The device of claim 1, wherein said milk-soluble agent is a polymer.

8. The device of claim 7, wherein said milk-soluble agent is at least one chosen from carrageenan, naphthalene sulfonate, or combinations thereof.

9. The device of claim 1, wherein said milk-soluble agent is efficacious against viruses.

10. The device of claim 9, wherein said milk-soluble agent is efficacious against HIV.

11. The device of claim 1, wherein said milk-soluble agent further includes a coloring agent.

12. The device of claim 1, wherein said matrix is non-soluble in milk.

13. The device of claim 1, wherein said matrix is a textile.

14. The device of claim 1, wherein said matrix is non-woven.

15. A device for preventing the transmission of disease during breastfeeding, said device comprising:

(a) an inlet for milk, said inlet defined by a breast shield;

(b) a therapeutic non-woven matrix downstream from said inlet, said matrix adapted to allow milk to pass through without significantly affecting the flow rate and being securely engaged with said breast shield by a retention lip formed by a circumferential protrusion of the breast shield located upstream of said matrix; and (c) an outlet downstream from said matrix, said outlet defined by said breast shield and suitable for suckling, wherein said matrix occupies substantially the entire cross section of said outlet.

16. The device of claim 15, wherein said matrix includes at least one therapeutic agent chosen from antivirals, anti-HIV agents, surfactants, alkyl sulfates, sodium dodecyl sulfate, polymers, naphthalene sulfonate polymer, carrageenan, anti-retroviral medicines, proteins, copper, copper derivatives and combinations of one or more.

17. The device of claim 15, wherein said matrix includes at least one substrate infused with at least one therapeutic agent.

18. The device of claim 15, wherein said matrix includes at least one therapeutic agent in a solid formation positioned adjacent to at least one substrate.

19. The device of claim 18, wherein said solid formation is irregularly shaped or perforated to facilitate desired speed of dissolution.

20. The device of claim 15, wherein said matrix further includes at least one additive chosen from colorants, flavorants, manufacturing aids, chemical stabilizers, structural stabilizers, shelf life extenders, environmental deterioration preventatives, dissolution rate regulators and combinations including at least one.

21. The device of claim 15, wherein said breast shield is adapted for a user to easily engage and disengage said matrix.

22. A method of delivering an agent into breast milk while breastfeeding comprising the acts of:

securing an agent-eluting matrix within the hollow nipple portion of a breast shield by engaging with a retention lip projecting inwardly into the nipple portion of said breast shield, wherein said matrix occupies substantially the entire cross section of said nipple portion;

positioning the breast shield on the breast of a lactating user; and allowing the intended recipient of said agent to suckle said breast shield.

23. The method of claim 22, wherein the act of securing includes the act of positioning said matrix past said retention lip.

24. The method of claim 22, wherein the act of securing further includes preceding act of selecting an agent-eluting matrix that exhibits at least one property chosen from disease prevention, disease treatment, antiparasitic, antimicrobial, antiviral, antiretroviral, anti-HIV, nutritionally beneficial and combinations including at least one.

25. The method of claim 22 further including the act of monitoring the matrix for indications of depletion of said agent.

26. The method of claim 22 further including the act of removing said matrix from said breast shield and retaining said breast shield for future usage.

27. A device for delivering an agent, said device comprising:

(a) a vehicle with a hollow nipple and a retention lip protruding inwardly into said hollow nipple; and (b) at least one matrix impregnated with at least one agent, said matrix positioned within said hollow nipple and secured by said retention lip, wherein said matrix occupies substantially the entire cross section of said nipple.

28. The device of claim 27, wherein said vehicle is a baby bottle or a pacifier.

29. The device of claim 27, wherein said vehicle and said matrix are readily separable.

30. The device of claim 27, wherein said retention lip is circumferentially positioned within said hollow nipple.

31. The device of claim 27, wherein said agent is Generally Recognized As Safe (GRAS).

32. The device of claim 27, wherein said agent is a surfactant.

33. The device of claim 32, wherein said agent is an alkyl sulfate.

34. The device of claim 32, wherein said agent is sodium dodecyl sulfate.

35. The device of claim 27, wherein said agent is a polymer.

36. The device of claim 35, wherein said agent is at least one chosen from carrageenan, naphthalene sulfonate, or combinations thereof.

37. The device of claim 27, wherein said agent is efficacious against viruses.

38. The device of claim 37, wherein said agent is efficacious against HIV.

39. The device of claim 27, wherein said agent includes at least one selected from orally administered pharmaceuticals, antibiotics, analgesics, CNS drugs, vitamins, minerals, micronutrients, probiotics, anti-retrovirals, proteins, copper, copper derivatives and combinations of one or more.

40. The device of claim 27, wherein said agent further includes a coloring agent.

41. The device of claim 27, wherein said matrix is a textile.

42. The device of claim 41, wherein said textile is a non-woven.

* * * * *